US011085910B2

(12) United States Patent
McNenly et al.

(10) Patent No.: US 11,085,910 B2
(45) Date of Patent: Aug. 10, 2021

(54) ULTRA-COMPACT SYSTEM FOR CHARACTERIZATION OF PHYSICAL, CHEMICAL AND IGNITION PROPERTIES OF FUELS

(71) Applicants:Matthew J. McNenly, Oakland, CA (US); Geoffrey M. Oxberry, Pleasanton, CA (US); Ahmed E. Ismail, Aachen (DE); Nicholas Killingsworth, Pleasanton, CA (US); Daniel L. Flowers, San Leandro, CA (US)

(72) Inventors: Matthew J. McNenly, Oakland, CA (US); Geoffrey M. Oxberry, Pleasanton, CA (US); Ahmed E. Ismail, Aachen (DE); Nicholas Killingsworth, Pleasanton, CA (US); Daniel L. Flowers, San Leandro, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 86 days.

(21) Appl. No.: 16/433,842

(22) Filed: Jun. 6, 2019

(65) Prior Publication Data
US 2019/0324009 A1 Oct. 24, 2019

Related U.S. Application Data

(62) Division of application No. 15/261,304, filed on Sep. 9, 2016, now Pat. No. 10,371,689.

(51) Int. Cl.
*G01N 33/28* (2006.01)
*F02D 19/06* (2006.01)
(Continued)

(52) U.S. Cl.
CPC ..... *G01N 33/2817* (2013.01); *F02D 19/0626* (2013.01); *F02D 19/0649* (2013.01);
(Continued)

(58) Field of Classification Search
USPC .......................................................... 702/30
See application file for complete search history.

(56) References Cited

U.S. PATENT DOCUMENTS

| 3,732,723 A | 5/1973 | Goolsby et al. |
| 3,982,878 A | 9/1976 | Yamane et al. |

(Continued)

OTHER PUBLICATIONS

Krueger, Hannes et al. "3D Printing of Magnetorheological Elastomers (MREs) Smart Materials", Proceedings of the 1st International Conference on Progress in Additive Manufacturing (Pro-AM 2014), pp. 213-218.

(Continued)

*Primary Examiner* — Paul D Lee
(74) *Attorney, Agent, or Firm* — Harness, Dickey & Pierce, P.L.C.

(57) ABSTRACT

The present disclosure relates to a miniaturized fuel laboratory system that makes use of a housing, a processor housed within the housing, and a fuel inlet port supported from the housing for receiving a quantity of fuel to be used as a fuel test sample. The system may also have at least one fuel sensor housed in the housing in communication with the fuel inlet port for receiving the fuel test sample and carrying out combustion thereof. An electronic component may be housed in the housing, which enables communication with an external remote subsystem. A database may be incorporated which contains at least one of stored fuel characteristics or stored fuel analysis models, accessible by the processor. The processor may use fuel oxidation information generated by the fuel sensor, and at least one of the stored (Continued)

Figure 1:
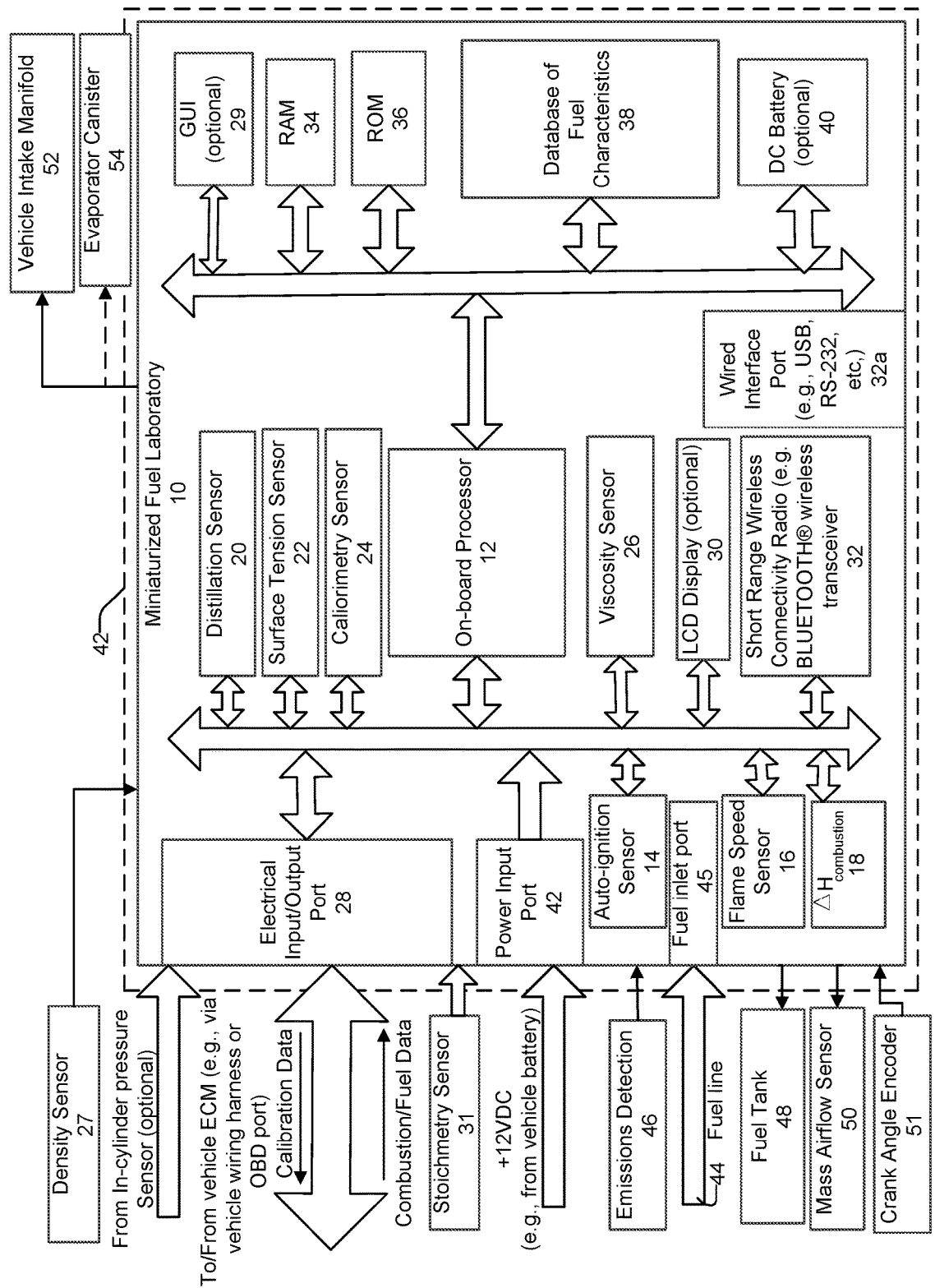

fuel characteristics or stored combustion models, to determine at least one fuel characteristic of the fuel test sample.

22 Claims, 2 Drawing Sheets

(51) Int. Cl.

| | | |
|---|---|---|
| G01K 17/00 | (2006.01) | |
| G06F 17/14 | (2006.01) | |
| G01K 17/14 | (2006.01) | |

(52) U.S. Cl.
CPC .............. *G01K 17/00* (2013.01); *G01K 17/14* (2013.01); *G06F 17/14* (2013.01); *Y02T 10/30* (2013.01)

(56) References Cited

U.S. PATENT DOCUMENTS

| | | | | |
|---|---|---|---|---|
| 4,283,256 | A * | 8/1981 | Howard | ................. G01N 31/12 |
| | | | | 123/703 |
| 4,848,133 | A | 7/1989 | Paulis et al. | |
| 6,312,154 | B1 | 11/2001 | Schick et al. | |
| 2002/0040593 | A1* | 4/2002 | Schaefer | .............. G01N 27/221 |
| | | | | 73/61.43 |
| 2002/0197955 | A1 | 12/2002 | Witkowski et al. | |
| 2008/0167823 | A1 | 7/2008 | Koehler et al. | |
| 2008/0264394 | A1 | 10/2008 | Spivak | |
| 2009/0188308 | A1 | 7/2009 | Krassinger et al. | |
| 2010/0211329 | A1* | 8/2010 | Farquharson | .......... G01N 21/84 |
| | | | | 702/28 |
| 2012/0022772 | A1 | 1/2012 | Miyamoto et al. | |
| 2012/0157725 | A1 | 6/2012 | McAuliffe | |
| 2014/0005881 | A1 | 1/2014 | Hardesty | |
| 2014/0229010 | A1* | 8/2014 | Farquharson | .......... G01N 33/22 |
| | | | | 700/272 |
| 2015/0346733 | A1 | 12/2015 | Yates et al. | |
| 2017/0089305 | A1 | 3/2017 | Jung | |

OTHER PUBLICATIONS

Lorang, David J. et al. "Photocurable Liquid Core-Fugitive Shell Printing of Optical Waveguides", Adv. Mater. 2011, pp. 1-4.

Deshmukh, Suraj S. and McKinley, Gareth H. "Adaptive Energy-Absorbing Materials Using Field-Responsive Fluid-Impregnated Cellular Solids", Smart Mater. Struct, 16 (2007), pp. 106-113.

Leonowicz, Marcin et al. "Rheological Fluids as a Potential Component of Textile Products", Fibres & Textiles in Eastern Europe 2014, 22, 1(103), pp. 28-33.

An International Historic Mechanical Engineering Landmark, The Waukesha CFR Fuel Research Engine, Waukesha Engine Division Dresser Industries Inc., Waukesha, Wisconsin 53187, Bulletin No. 1163, Jun. 1980, 16 pages; https://www.asme.org/getmedia/ffedc33f-7e2b-4775-95ec-2f633ddc16f6/50-Cooperative-Fuel-Research-Engine-1928.aspx.

\* cited by examiner

ULTRA-COMPACT SYSTEM FOR CHARACTERIZATION OF PHYSICAL, CHEMICAL AND IGNITION PROPERTIES OF FUELS

CROSS-REFERENCE TO RELATED APPLICATIONS

This application is a divisional of U.S. patent application Ser. No. 15/261,304 filed on Sep. 9, 2016, and presently allowed. The entire disclosure of the above application is incorporated herein by reference.

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to fuel analyzers, and more particularly to a miniaturized fuel analyzer well suited to be used with an extremely small fuel sample either in a laboratory environment or as a hand held device, or integrated into any type of fuel-driven component or system, and well suited for use with all types of combustion engine powered vehicles or devices, for more efficiently analyzing and determining a plurality of properties of a fuel being used with the vehicle to optimize engine performance and/or emissions reduction.

BACKGROUND

This section provides background information related to the present disclosure which is not necessarily prior art.

Demand for transportation fuels is predicted to grow at a faster rate than energy use in any other sector over the next 25 years as the economies of developing nations grow. Diversifying the pool of transportation fuels is necessary to offset the many problems associated with increased demand. Alternative fuels, such as biofuels, can reduce greenhouse gas emissions and, if domestically sourced, can provide increased energy security. New engine technologies and combustion regimes being developed to reduce emissions and increase engine efficiency are changing the combustion process within engines. These new engines can greatly benefit from fuels that are optimized for use in them.

The development and production of new fuels is typically done in a laboratory setting, making it difficult and costly to produce large quantities of fuel. One of the most important fuel characteristics for diesel engines is its ignition quality, which gives some indication of how readily the fuel autoignites. Current ignition characterization tests require large amounts of fuel and very specialized and expensive equipment. The ignition quality of diesel fuel is characterized by the cetane number, which is based on testing the fuel in a Cooperative Fuels Research (CFR) engine (see, e.g., https://www.asme.org/getmedia/ffedc33f-7e2b-4775-95ec-2f633ddc16f6/50-Cooperative-Fuel-Research-Engine-1928.aspx).

The CFR engine is an engine that was originally developed in 1929 specifically for fuels testing. Operation of the CFR engine with the test fuel is compared to operation with a mixture of two standard fuels (cetane and isocetane, also known as n-hexadecane and 2,2,4,4,6,8,8-Heptamethylnonane, as defined in ASTM D-613). The percentage of cetane in the mixture that gives comparable operation defines the cetane number of the test fuel.

Recently, the ignition quality tester (IQT) was developed to decrease the testing effort and the volume of fuel required for determining the ignition quality of a given test fuel. In this test, fuel is injected into a constant volume chamber filled with air at high pressure and temperature; the time between injection of the fuel and the occurrence of ignition is then used to determine the derived cetane number of the test fuel as defined in ASTM D-6890. This method requires on the order of 100 ml of fuel, which can still be a prohibitively large quantity for fuels generated in a research laboratory.

Another issue with CFR and IQT ignition quality tests is that they make use of legacy injection technology. The ignition delay determined in an engine or the IQT is a function of the time for the fuel to evaporate and mix, as well as a chemical time-delay. The older injection technology found in these legacy tests uses lower injection pressures, producing larger fuel droplets than today's high pressure common rail injection systems. Therefore, the vaporization time delay in these tests is inconsistent with that found in engines using modern injection technology.

The cetane number enables comparison of diesel fuel from all over the globe, and its allowable range can vary greatly from country to country. This variation is an issue for vehicles that are calibrated with a particular standard cetane number in one country and then moved to a country with a different standard (if that particular country even has a standard at all). This situation occurs often in the military, which uses vehicles all over the world and must deal with large variations in fuel quality. Operating a diesel engine with fuel that differs in cetane number from the engine's baseline calibration fuel can lead to decreased engine efficiency, increased harmful emissions, failure to achieve fuel ignition, or even engine damage.

On-board fuel characterization would improve operation of engines when fuel properties vary from the baseline fuel that the engine is calibrated for. The engine control unit (ECU) could be updated with information about fuel ignition quality that is currently in the vehicle's tank and make appropriate corrections to the injection timing, exhaust gas residuals, or other engine parameters, resulting in more efficient operation and cleaner (i.e., reduced emissions) operation. An engine equipped in this manner could then readily deal with a range of fuels, including biofuels, despite being calibrated with a different fuel. This flexibility has especially significant implications for military vehicles that see wide-ranging fuel variation from country-to-country, as well as the normal variations that occur season-to-season in the United States, and from region-to-region within the United States at a given time of year.

Similar to the cetane number used to characterize diesel fuel, the octane number is used to characterize fuel for spark-ignited engines. The CFR engine is also used to determine a fuel's octane number in ASTM D-2699 and ASTM D-2700. The issues that make testing new diesel fuels difficult and costly also plague fuels for spark-ignited engines. There is a similar need to develop new methods of testing properties of fuels for spark-ignited engines that require low volumes of fuel and can be carried out in real time on-board the vehicle.

SUMMARY

This section provides a general summary of the disclosure, and is not a comprehensive disclosure of its full scope or all of its features.

In one aspect the present disclosure relates to a miniaturized fuel laboratory system. The system may comprise a housing, a processor housed within the housing, and a fuel inlet port supported from the housing for receiving a quantity of fuel to be used as a fuel test sample. The system may also include at least one fuel sensor housed in the housing in communication with the fuel inlet port for receiving the fuel test sample. An electronic input/output communications port may be included which is housed in the housing, and which enables bidirectional, electronic communication with an external, remote subsystem. A database may be incorporated which contains at least one of stored fuel characteristics or stored fuel analysis models, accessible by the processor. The processor may use information obtained by the fuel sensor and at least one of the stored fuel characteristics or stored fuel analysis models, to determine at least one fuel characteristic of the fuel test sample.

In another aspect the present disclosure relates to a miniaturized, hand holdable fuel laboratory system. The system may include a housing, a processor housed within the housing, a fuel inlet port supported from the housing for receiving a quantity of fuel to be used as a fuel test sample, and at least one fuel sensor housed in the housing. The fuel sensor may be in communication with the fuel inlet port for receiving the fuel test sample. An electronic input/output communications port may be included which is housed in the housing and which enables bidirectional, electronic communication with an external, remote subsystem. At least one port may be included which is configured to receive available information from a remote component associated with an internal combustion engine. A database containing stored fuel characteristic information may also be included which is accessible by the processor. The processor may use information obtained by at least a subplurality of the fuel sensor, the database and the information from the remote component, to determine at least one measured fuel characteristic of the fuel test sample.

In still another aspect the present disclosure relates to a miniaturized, hand-holdable fuel laboratory system. The system may comprise a housing, a processor housed within the housing, a fuel inlet port supported from the housing for receiving a quantity of fuel to be used as a fuel test sample, and at least one fuel sensor housed in the housing in communication with the fuel inlet port for receiving the fuel test sample. The at least one sensor may comprise a plurality of different sensors from a group including: a calorimetry sensor for measuring a chemical energy released by fuel and oxidizer mixtures, including at least one of an increased heating value or a decreased heating value; a heat of combustion sensor which senses an amount of heat energy released during combustion of a fuel-oxidizer mixture; an auto-ignition sensor for measuring a time which it takes for a premixed volume of fuel and oxidizer to spontaneously ignite at a given initial temperature and pressure; a viscosity sensor for measuring an internal friction or resistance of parallel layers of fluid moving at different speeds for the fuel text sample; a distillation curve sensor for measuring a volume of liquid in a mixture that has evaporated at a given temperature, and providing information regarding at least one of a boiling point temperature or enthalpy of vaporization; and a surface tension sensor for measuring a resistive force of a surface film of a liquid caused by an attraction of molecules in a surface layer by a bulk of the liquid, which tends to minimize surface area. An electronic input/output communications port may be included which is housed in the housing and which enables bidirectional, electronic communication with an on-board diagnostic port of a vehicle having an internal combustion engine. At least one port may be included which is configured to receive information from a sensor associated with an internal combustion engine. A database containing stored fuel characteristic information accessible by the processor may also be included. The processor may use information obtained by the fuel sensor, the database, and the information from the remote sensing component, to determine at least one fuel characteristic of the fuel test sample.

DRAWINGS

The drawings described herein are for illustrative purposes only of selected embodiments and not all possible implementations, and are not intended to limit the scope of the present disclosure.

Figure 2:
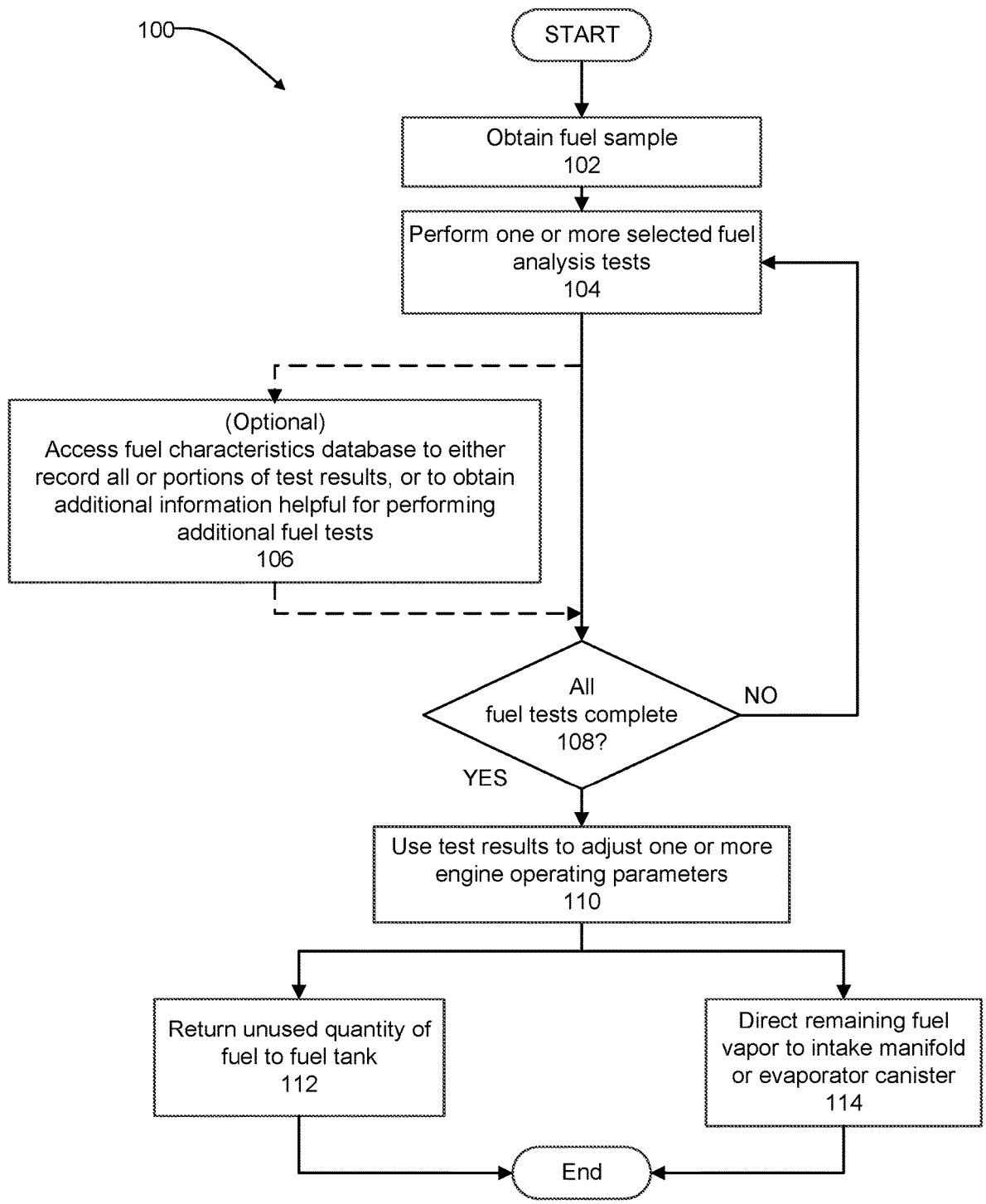

FIG. 1 is a high-level block diagram of a miniaturized fuel laboratory system suitable for inclusion in a hand-held enclosure or integrated into an engine compartment of a motor vehicle; and FIG. 2 is a high-level flowchart illustrating various operations that may be performed by the system of FIG. 1.

Corresponding reference numerals indicate corresponding parts throughout the several views of the drawings.

DETAILED DESCRIPTION

Example embodiments will now be described more fully with reference to the accompanying drawings.

The present system and method relates to a miniaturized fuel sensor having a form factor making it either hand-holdable or readily integrated into a fuel-burning component. The system enables performing real time fuel analysis of the fuel being used by an engine of the fuel burning component, and also providing useful information on a plurality of characteristics and/or properties of the fuel to a different subsystem, for example an engine control unit (ECU), which can be used by the subsystem to help tailor one or more operating parameters of the engine. While the system is ideally suited to be used with, or integrated into, an engine of a piston-engine-driven land vehicle such as an automobile, truck, van, motorcycle, all-terrain vehicle, snow mobile, or earth moving equipment, the system of the present disclosure may also be used with, or integrated into, a wide variety of other vehicles and fuel burning devices. Such other vehicles may include aircraft, rotorcraft and watercraft, whether manned or unmanned. Other fuel burning devices may include piston-engine-driven electrical power generators. The system and method is therefore useable with virtually any type of fuel-powered vehicle or fuel-powered device which makes either full time or part time use of a piston engine, and for which a quality of the fuel being supplied, or the characteristics of the fuel, needs to be determined.

In one embodiment, the system relates to a miniaturized fuel laboratory that is ideally suited to be included in a hand-held enclosure, and which incorporates a set of sensors, for example a set of "on-chip" sensors provided on one printed circuit board assembly, or a plurality of interconnected circuit board assemblies, or on an application specific integrated circuit ("ASIC"), that characterize liquid fuels such that their behavior in internal combustion engines can be analyzed, estimated and/or predicted. One or more of the following properties may be measured from an extremely small fuel test sample, which may be on the order of 100 milliliters or less, in order to characterize the fuel. The characterization of the fuel may involve one or more fuel parameters such as: heat of combustion; density; vapor pressure; vapor recovery during distillation; viscosity; temperature; surface tension; rate of droplet evaporation; ignition delay of a homogenous fuel-air mixture; ignition delay of a fuel droplet, including vaporization, mixing with oxidizer, and ignition; thermal diffusion; mass diffusion; laminar flame speed; and flame stretch; chemical composition; and molecular structure. Measurement of these properties provides a detailed characterization of the fuel and, as noted above, requires only a minimal volume of fuel for performing the analysis. An array of sensors corresponding to these measurements may be used at various temperatures and pressures such that the behavior of the fuel in an engine can be estimated. Empirical and physics-based analysis may be used to relate measured data to various fuel properties. Furthermore, physics-based models and engine geometry may be used to estimate how a given fuel behaves in the engine with which it is being used. This information can be used by the vehicle's engine control unit (ECU) to adjust the engine over a wide range of different engine operating parameters to deal with variation in fuel properties and thus optimize fuel economy and/or optimize emissions reductions. These tests may be performed every time the fuel tank of the vehicle is filled up, at regular time or mileage intervals, on-demand by the ECU or even on a command given by the driver, or continuously, substantially in real time.

The method may involve running the engine under various conditions so that the fuel can be fully characterized. A minimal fueling rate may be used for the first part of the test to minimize the occurrence of damage to the engine and increased in a controlled fashion. Various inlet conditions, injection timings, and fuel mass fractions may be used to characterize the fuel over a large range of parameters. These tests may be performed every time the fuel tank is filled up, at regular time or mileage intervals, on-demand by the engine controller or by the driver, or continuously.

The information about the fuel obtained from the various embodiments and methods described above may be used "on-vehicle" by the vehicle's ECU to change various operating parameters, thus allowing better operation of the engine, either from a fuel efficiency standpoint, an emissions reduction standpoint, or both. The various embodiments discussed herein could also be implemented in a stand-alone, miniaturized fuel analyzer which is well suited for use in laboratory and industrial settings as a more cost effective alternative to the standard fuel characterization test methods, which typically employ physically large and costly analytical equipment.

Referring now to FIG. 1, a miniaturized fuel laboratory system 10 (hereinafter simply "system 10") is shown in accordance with one embodiment of the present disclosure. The system 10 in this example may include an on-board computer processor 12 that communicates with a large plurality of sensors which sense various characteristics of a fuel. The processor 12 may incorporate a microprocessor and may make use of suitable software and firmware for controlling the various operations performed by the processor 12.

The fuel may be sensed and characterized for a diesel engine, for a spark ignited engine or for any another application or device (e.g., piston engine driven electrical power backup generator). The sensors used to sense various characteristics and properties of the fuel may include, but are not limited to, one or more of the following: an auto-ignition sensor 14; a flame speed sensor 16; a heat of combustion sensor 18; a distillation curve sensor 20; a surface tension sensor 22; a calorimetry sensor 24; a viscosity sensor 26, a density sensor 27 and a stoichiometry sensor 31. The processor 12 may also be in communication with an electrical input/output port 28, an optional graphical user interface (GUI) 29; an optional display (e.g., LCD display) 30 which may be a part of, or independent of, the GUI 29, a short range wireless radio (e.g., BLUETOOTH® wireless transceiver) 32 for communicating wirelessly with a personal electronic device of a user (e.g., computing tablet; laptop, PDA, smartphone, etc.), and a wired interface port 32a (e.g., USB, RS-232, RS-422, etc.) to enable a wired connection with a personal electronic device. If the GUI 29 is incorporated, this may enable the user to initiate a fuel analysis operation manually.

The processor 12 may also be in communication with a random access memory 34, a read only memory 36, and an optional fuel characteristics database 38. An optional DC rechargeable or non-rechargeable battery 40 may be included if the system 10 is provided in a hand-holdable enclosure 42 for stand-alone use. Otherwise, if the system is integrated into the engine compartment of the vehicle, a power input port 42 may be provided to receive power, either AC or DC, from a power source associated with the vehicle or device. With many civilian or military purpose vehicles, +12 VDC, +24V or other voltage signal is commonly available from the vehicle's wiring harness. This signal may be used to power the device or it may be regulated down to a different voltage, for example, +5 VDC, by well-known voltage regulation circuitry associated either with the vehicle's or device's electronics, or by well-known regulator circuitry (not shown) included in the system 10.

The system 10 is coupled for bidirectional electrical communications to the vehicle's wiring harness (not shown), or if used as a stand-alone system within the housing 42, it may be removably coupled to the vehicle's OBD (on-board diagnostic port) to enable bidirectional electrical communications with all of the vehicle's sensors and subsystems that communicate on the vehicle's communications bus (i.e., typically a Controller Area Network (CAN) bus). In either configuration, the system 10 may include an input port for receiving a small quantity of fuel, typically about 100 milliliters or less, and more typically about 1 ml or less, from the vehicle's fuel line 44 for use in its analysis, as well as signals from the vehicle's emissions detection subsystems 46. While not shown explicitly in FIG. 1, it will be appreciated that the fuel inlet port 45 is in communication with inputs of each of the above-described sensors to enable each sensor to access a portion of the small fuel sample received by the system 10. Any small amount of fuel which exists after testing and analysis may be returned to the vehicle's fuel tank 48. It is also possible that for an on-board vehicle application, one or more of the sensors of the system 10 may be remotely located at one or more of a vehicle fuel tank, a fuel line associated with the fuel tank, at a location in the fuel system such as a fuel line feeding a fuel pump or a fuel line at an output of the fuel pump (i.e., after pressurization), at a fuel line leading to each cylinder's injector, or in a return line from each injector. It is also possible to implement cylinder-by-cylinder analysis of fuel characteristics for control purposes.

The results of the fuel analysis performed by the system may be used to control a wide variety of engine variables by suitable control signals applied to one or more of the engine's subsystems. For example, the results of a fuel analysis operation may be used to modify mapping of a mass air flow sensor 50 to change the air/fuel ratio being used by the engine, to change valve timing in an engine having variable valve timing capability, to adjust spark timing (either advance or retard spark timing), fuel injection timing (number of injection pulses per cycle and per cylinder, start of each injection, end of each injection, rate shape profile for each injection event), fuel injector pressure, a wastegate of a turbocharged engine, boost pressure of a supercharged or turbocharged engine, intake valve timing (opening, closing, lift profile), exhaust valve timing (opening, closing, lift profile), internal and external exhaust gas recirculation (EGR), or coolant temperature. It is also possible that multiple fuels could be available for an engine, and the mixture of fuel from each fuel tank could be tuned based on individual fuel characteristics or mixture characteristics on a cylinder-by-cylinder basis. Control of one or more of the above variables may help to avoid engine knock or possibly excessively high engine coolant temperatures. Any vaporized or oxidized fuel may be directed to the vehicle's intake manifold 52 or returned to the vehicle's evaporative emissions canister 54.

The various sensors of the system 10, as mentioned above, may perform the following operations:

Auto-ignition sensor 14: measures the time it takes for a premixed volume of fuel and oxidizer to spontaneously ignite at a given initial temperature and pressure. Where the ignition time can be associated with the time at which there is a large change in the pressure, temperature, or heat release rate of the mixture.

Flame Speed Sensor 16: measures a propagation of a flame front while a fuel and an oxidizer are consumed in a flame. Example sources of this measurement include, but are not limited to, laminar flame propagation in a tube or duct, and turbulent flame propagation inferred from one or more of the engine speed, spark plug timing, exhaust temperature, and the knock sensor.

Heat of Combustion ($\Delta_{combustion}H$) Sensor 18: senses the amount of heat energy released during combustion of a fuel-oxidizer mixture with the formation of complete products.

Distillation Curve Sensor 20: measures the volume of liquid in a mixture that has evaporated at a given temperature. The distillation curve provides information regarding the boiling point, enthalpy of vaporization (i.e., the amount of energy needed to go from liquid to gas phase), vapor pressure, and the molecular composition.

Surface Tension Sensor 22: measures the resistive force of the surface film of a liquid caused by the attraction of the molecules in the surface layer by the bulk of the liquid, which tends to minimize surface area.

Calorimetry Sensor 24: measures the total chemical energy released by fuel and oxidizer mixtures.

Viscosity Sensor 26: measures the internal friction or resistance of parallel layers of fluid moving at different speed for the fuel. This can be inferred by measuring the flow rate and pressure through a known duct geometry.

Density Sensor 27: senses the density of the fuel.

Stoichiometry Sensor 31: measures the mass of oxidizer needed to completely consume a given mass of fuel.

Similar sensors to the calorimetry, viscosity and density sensors 24, 26 and 27, respectively, may be needed for the oxidizer (i.e., evaporator canister 54 or a separate oxidizer). In current engines, these quantities for the oxidizer are estimated from temperature and mass flow sensors.

The fuel characteristics database 38, while optional, may be used to hold one or more measured fuel characteristics that have been obtained by the system 10 over a period of time (e.g., weeks or months). The database may contain information about the fuel, suggested engine inputs, or expected engine performance given various fuel parameters. The database may come prepopulated or may be connected wirelessly to the cloud and receive information from other engines or instances of system 10 in other vehicles. Furthermore analysis/calculations may be carried out on-board system 10 or they could be carried out in the cloud and relayed to system 10. The database may contain information to compute/model/estimate any fuel characteristics not directly measured by the system. For example, this could include tables of previously measured transport and thermodynamic properties (e.g., from JANAF and NIST data). It could also include data necessary to perform real-time simulations of the fluid or chemistry phenomena. For example, real time simulations may involve using chemical kinetic ignition calculations as reference data to determine ignition timing.

The system 10 may also use the engine of the vehicle to help determine various characteristics of the fuel or various engine performance aspects that depend on the quality or characteristics of the fuel. More particularly, the system 10 may be used to help control the engine itself, in an effort to determine various specific properties of the fuel being used with the engine. The system 10 and method of the present disclosure may determine the fuel characteristics within the cylinder and relate it to fuel injection in compression ignition engines or spark timing in spark-ignited engines. Analysis of a crank angle encoder signal obtained by a crank angle encoder 51 (FIG. 1) may be used to relate the timing of various events as well. For example, the system 10 may employ control over the engine to predict the instantaneous torque produced by the combustion process. Signal processing may then be used to relate this timing back to the engine's ECU (Engine Control Unit) to help control the combustion process. Alternatively, the crankshaft encoder could be used in conjunction with an in-cylinder pressure transducer to determine characteristics of the combustion process. A model of the combustion process including engine geometry may then be used to determine the fuel properties based on the measured in-cylinder processes. The use of a physics-based, empirical, or adaptive model of the engine combustion process to determine the properties of the fuel differentiates this method from previous fuel analysis systems. The use of physics-based models increases the accuracy of the methods described herein and helps to remove dependency on engine hardware for performing the fuel composition tests.

Referring to FIG. 2, a high level flow chart 100 is shown of various operations that may be performed by the system 10 in analyzing a fuel sample. As mentioned above, the fuel sample may be obtained after fuel has been added to the vehicle's gas tank, or possibly each time the vehicle is started, or possibly periodically every so many minutes or miles of vehicle operation, or even substantially continuously in substantially real time. At operation 102 a fuel sample is initially obtained by the system 10. Fuel may be obtained by opening a small solenoid valve in the fuel line to divert a very small quantity of fuel into the system 10. At operation 104 the system 10 may perform one or more selected fuel analysis tests, as described herein. Optionally, the fuel characteristics database 38 may be accessed to obtain additional information that may be helpful in the fuel analysis process, or to write all or portions of the test results of the just-performed test to the database. A check is then made if all of the fuel tests are complete, as indicated at operation 108. If not, operation 104 is repeated. If all fuel tests are complete, then at operation 110 the system 10 may use the test results to adjust one or more engine operating parameters in an effort to optimize either fuel economy, engine performance (e.g., torque output) or emissions reduction, or a combination of these factors. Any portion of unused fuel collected by the system 10 may be returned to the vehicle's fuel tank 48, as indicated at operation 112, or possibly directed to the intake manifold 52 or the vehicle's evaporative emissions canister 54.

For each of the various embodiments discussed, it will be appreciated that the term "sensor" may not only refer to a physical device directly measuring the quantity of interest, but it may also relate to a virtual sensor. A virtual sensor may exist when which the quantity or parameter of interest is inferred from one, two or more other physical sensors on the vehicle. And as noted above, the system 10 need not necessarily incorporate every single sensor shown in FIG. 1, and conversely, the system 10 may incorporate other sensors that are not explicitly shown in FIG. 1. As such, FIG. 1 is not intended to be an exhaustive illustration of all the different types of sensors that may be used to help form the system 10, and thus to help improve the engine performance (e.g., engine efficiency, engine power, engine emissions, or engine reliability). It is also possible that a variant of the system 10 could be used for gaseous fuels, for example natural gas. It will also be appreciated that for the various embodiments of the system 10 described herein, an additional fuel filter beyond the standard fuel filter in the fuel system may be helpful to avoid clogging due to the small dimensions of the various sensors described herein, and due to the possible sensitive nature of these the various sensors described herein.

The system 10 and the various methods of the present disclosure provide the capability to quickly determine important characteristics of the fuel being used with a vehicle. Importantly, the system 10 is able to function essentially as an on-board fuel laboratory using extremely small quantities of fuel, typically on the order of 0.1% to 5% of what would be needed for analysis with a laboratory fuel analyzer. The system 10 may be integrated into a hand-holdable housing or integrated into the vehicle's engine. And while the system 10 and method has been described in connection with a motor vehicle such as an automobile or truck, it will be appreciated that the system may be used with any type of vehicle requiring either a diesel or spark ignited fuel for its operation. The system 10 is expected to be especially useful in military operations where motorized military land, air and sea vehicles need to be used all over the world, and thus will need to be operated on fuels having widely varying characteristics. The system 10 is also expected to find utility with stationary diesel and gasoline powered engines and devices, as well as with gas turbines. The system 10 may also be integrated into a fuel pump at a fuel station to analyze a fuel and to wirelessly communicate with a vehicle's ECU to inform the ECU of the characteristics of the fuel being delivered to the vehicle's fuel tank. The system 10 may also find utility in stationary applications such as fuel refineries, power plants (e.g., oil or gas-fired), with ovens/combustors (e.g., for smelting, ceramics manufacture), and for fuel cells, which could be stationary or mobile, depending on the application.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A miniaturized fuel laboratory system, the system comprising:
    a housing;
    a processor housed within the housing;
    a fuel inlet port supported from the housing for receiving a quantity of fuel to be used as a fuel test sample;
    at least one fuel sensor housed in the housing in communication with the fuel inlet port for receiving the fuel test sample, the fuel sensor operating to carry out combustion of the fuel test sample to generate information relating to fuel oxidation of the test sample, for subsequent use in predicting a performance of the quantity of fuel in an internal combustion engine;
    a communications component housed in the housing enabling communication with an external remote subsystem;
    a database containing at least one of stored fuel characteristics or stored fuel analysis models, accessible by the processor; and
    the processor using the information relating to fuel oxidation together with the stored fuel characteristics or stored fuel analysis models, to help predict the performance of the quantity of fuel in the internal combustion engine.

2. The system of claim 1, wherein the communications component comprises an electronic input/output communications port enabling communication with an electronic control module (ECM) of a vehicle.

3. The system of claim 2, wherein the processor is configured to use the information pertaining to fuel oxidation to assist the ECM in controlling at least one of:
    mapping of a mass air flow sensor to change an air/fuel ratio being used by an engine of the vehicle;
    valve timing and lift profile of a valve train of the engine;
    spark timing and ignition energy for the engine;
    injection characteristics on each injector of each cylinder of an engine, including number of injections, timing for each injection, and a profile of each injection event;
    fuel injector pressure for the engine;
    a wastegate of a turbocharger of the engine;
    boost of a turbocharger of the engine;
    boost of a supercharger of the engine; and
    engine temperature set-point.

4. The system of claim 1, wherein the system further comprises a distillation curve sensor for measuring a volume of liquid in a mixture that has evaporated at a given temperature, and providing information regarding at least one of a boiling point temperature or enthalpy of vaporization.

5. The system of claim 1, further comprising a surface tension sensor for measuring a resistive force of a surface film of a liquid caused by an attraction of molecules in a surface layer by a bulk of the liquid, which tends to minimize surface area.

6. The system of claim 1, further comprising a calorimetry sensor for measuring a chemical energy released by fuel and oxidizer mixtures, including at least one of an increased heating value or a decreased heating value.

7. The system of claim 1, wherein the at least one fuel sensor comprises a flame speed sensor for measuring a propagation of a flame front while a fuel and an oxidizer are consumed in a flame.

8. The system of claim 1, wherein the at least one fuel sensor comprises at least one of:
    a heat of combustion sensor which senses an amount of heat energy released during combustion of a fuel-oxidizer mixture; or
    a auto-ignition sensor for measuring a time which it takes for a premixed volume of fuel and oxidizer to spontaneously ignite at a given initial temperature and pressure.

9. The system of claim 1, further comprising a viscosity sensor for measuring an internal friction or resistance of parallel layers of fluid moving at different speeds for the fuel test sample.

10. The system of claim 1, wherein the system is configured to discharge an unused portion of the fuel test sample which has been analyzed from the system.

11. The system of claim 1, wherein the system is configured to direct a vapor-phased fuel sample, vaporized portion of an initially liquid fuel sample, or oxidized fuel sample which has been analyzed to at least one of an intake manifold and an evaporative emissions canister associated with the engine of a vehicle.

12. The system of claim 1, wherein the communications component comprises a short range wireless radio for enabling the system to make a wireless communications link with the external remote subsystem.

13. The system of claim 1, further comprising a power input port for receiving at least one of:
    an external direct current (DC) signal to power the system; or
    an external alternating current (AC) signal to power the system.

14. The system of claim 1, wherein the system includes an input for receiving at least one of:
    information on a crank angle from a crank angle encoder associated with an engine of a vehicle;
    information from an emissions related component of a vehicle; and
    information from an in-cylinder pressure sensor of a vehicle, wherein the in-cylinder pressure sensor senses a pressure within a cylinder of an engine of the vehicle.

15. The system of claim 1, wherein the system comprises an output for outputting an electrical signal to a mass air flow sensor of a vehicle.

16. The system of claim 1, wherein the system comprises an input for receiving information from at least one of:
    a fuel density sensor; or
    a stoichiometry sensor.

17. A miniaturized, hand holdable fuel laboratory system, the system comprising:
    a housing;
    a processor housed within the housing;
    a fuel inlet port supported from the housing for receiving a quantity of fuel to be used as a fuel test sample;
    at least one fuel sensor housed in the housing in communication with the fuel inlet port for receiving the fuel test sample, the test fuel sample forming a quantity of fuel no greater than 100 milliliters;
    a communications component housed in the housing and enabling bidirectional communication with an external remote subsystem;
    at least one port configured to receive available information from the external remote subsystem, and wherein the external remote subsystem is associated with an internal combustion engine;

a database containing stored fuel characteristic information accessible by the processor;

the processor using information obtained by at least a subplurality of the fuel sensor, the database and the information from the external remote subsystem, to determine at least one measured fuel characteristic of the fuel test sample.

18. The system of claim 17, wherein the processor in configured to use information obtained from the database, the information obtained from the external remote subsystem, and information from the fuel sensor, to determine the at least one fuel characteristic of the fuel test sample.

19. The system of claim 17, wherein the at least one fuel sensor comprises at least one of:
   a calorimetry sensor for measuring a chemical energy released by fuel and oxidizer mixtures, including at least one of an increased heating value or a decreased heating value;
   a heat of combustion sensor which senses an amount of heat energy released during combustion of a fuel-oxidizer mixture;
   an auto-ignition sensor for measuring a time which it takes for a premixed volume of fuel and oxidizer to spontaneously ignite at a given initial temperature and pressure;
   a viscosity sensor for measuring an internal friction or resistance of parallel layers of fluid moving at different speeds for the fuel test sample;
   a distillation curve sensor for measuring a volume of liquid in a mixture that has evaporated at a given temperature, and providing information regarding at least one of a boiling point temperature or enthalpy of vaporization; or
   a surface tension sensor for measuring a resistive force of a surface film of a liquid caused by an attraction of molecules in a surface layer by a bulk of the liquid, which tends to minimize surface area.

20. The system of claim 17, wherein the at least one port configured to receive information from the remote subsystem comprises:
   a port to receive information from a fuel density sensor;
   a port to receive information from a stoichiometry sensor;
   a port to receive information regarding a crank angle from a crank angle encoder associated with an engine of a vehicle;
   a port to receive engine emissions information from a computer associated with an engine of a vehicle; or
   a port to receive information from an in-cylinder pressure sensor of an engine of a vehicle.

21. A miniaturized, hand-holdable fuel laboratory system, the system comprising:
   a housing;
   a processor housed within the housing;
   a fuel inlet port supported from the housing for receiving a quantity of fuel to be used as a fuel test sample;
   at least one fuel sensor housed in the housing in communication with the fuel inlet port for receiving the fuel test sample, the at least one sensor comprising a plurality of:
      a flame speed sensor which measures a flame speed during combustion of the fuel test sample;
      a calorimetry sensor for measuring a chemical energy released by fuel and oxidizer mixtures, including at least one of an increased heating value or a decreased heating value;
      a heat of combustion sensor which senses an amount of heat energy released during combustion of a fuel-oxidizer mixture;
      an auto-ignition sensor for measuring a time which it takes for a premixed volume of fuel and oxidizer to spontaneously ignite at a given initial temperature and pressure;
      a viscosity sensor for measuring an internal friction or resistance of parallel layers of fluid moving at different speeds for the fuel test sample;
      a distillation curve sensor for measuring a volume of liquid in a mixture that has evaporated at a given temperature, and providing information regarding at least one of a boiling point temperature or enthalpy of vaporization; and
      a surface tension sensor for measuring a resistive force of a surface film of a liquid caused by an attraction of molecules in a surface layer by a bulk of the liquid, which tends to minimize surface area;
   an electronic input/output communications port housed in the housing enabling bidirectional, electronic communication with an on-board diagnostic port of a vehicle having an internal combustion engine;
   at least one port configured to receive information from a sensor associated with an internal combustion engine;
   a database containing stored fuel characteristic information accessible by the processor;
   the processor using information obtained by the fuel sensor, the database and the information from the sensor associated with the internal combustion engine, to determine at least one fuel characteristic of the fuel test sample.

22. A method for forming a hand-holdable fuel laboratory system, the method comprising:
   using a housing to house a processor, a fuel inlet port for receiving a quantity of fuel to be used as a fuel test sample, at least one fuel sensor housed in the housing in communication with the fuel inlet port for receiving the fuel test sample and carrying out combustion of the fuel test sample, and a communications component housed in the housing enabling receipt of information from an external remote subsystem;
   using a database in communication with the processor to store at least one of fuel characteristics or fuel analysis models, accessible by the processor; and
   causing the processor to use fuel oxidation information generated by the fuel sensor and at least one of the stored fuel characteristics or stored fuel analysis models, to determine at least one fuel characteristic of the fuel test sample.

* * * * *